(12) United States Patent
Lund-Jensen et al.

(10) Patent No.: US 7,435,398 B2
(45) Date of Patent: Oct. 14, 2008

(54) APPARATUS FOR STERILIZING DENTAL HAND PIECES

(75) Inventors: Jesper Wenzel Lund-Jensen, Silkeborg (DK); Mads Nørby, Galten (DK)

(73) Assignee: Nitram Dental A/S, Risskov (DK)

( * ) Notice: Subject to any disclaimer, the term of this patent is extended or adjusted under 35 U.S.C. 154(b) by 200 days.

(21) Appl. No.: 10/986,436

(22) Filed: Nov. 12, 2004

(65) Prior Publication Data

US 2006/0104875 A1   May 18, 2006

(51) Int. Cl.
*A61L 2/00* (2006.01)
*A61L 9/00* (2006.01)

(52) U.S. Cl. .................. 422/298; 422/292; 422/295; 422/297

(58) Field of Classification Search .................. 422/298, 422/297; 403/168; 48/191, 194; 55/419; 74/427; 96/60; 134/170, 171
See application file for complete search history.

(56) References Cited

U.S. PATENT DOCUMENTS

| | | | | |
|---|---|---|---|---|
| 4,686,837 A * | 8/1987 | Carre | ............................ | 24/705 |
| 4,922,199 A * | 5/1990 | Fukui et al. | ............. | 324/207.17 |
| 4,991,582 A * | 2/1991 | Byers et al. | ...................... | 607/2 |
| 5,164,272 A * | 11/1992 | Lowton et al. | ................ | 429/104 |
| 5,239,729 A * | 8/1993 | Scholl | ........................... | 16/257 |
| 5,520,892 A * | 5/1996 | Bowen | ......................... | 422/295 |
| 5,552,113 A | 9/1996 | Jennings | | |
| 5,723,090 A * | 3/1998 | Beerstecher et al. | ........... | 422/26 |
| 5,880,438 A * | 3/1999 | Parrini et al. | ................. | 219/519 |
| 6,379,614 B1 * | 4/2002 | Sergio et al. | ................... | 422/28 |
| 6,773,685 B2 * | 8/2004 | Johansen | ...................... | 422/295 |
| 2002/0044898 A1 * | 4/2002 | Sergio et al. | ................. | 422/300 |
| 2002/0068029 A1 * | 6/2002 | Johansen | ..................... | 422/297 |
| 2004/0001783 A1 * | 1/2004 | Bowen | ......................... | 422/292 |
| 2005/0236230 A1 * | 10/2005 | Fee | ............................. | 184/55.2 |
| 2006/0251540 A1 * | 11/2006 | Benning et al. | ................. | 422/3 |

FOREIGN PATENT DOCUMENTS

| | | | |
|---|---|---|---|
| DE | 29915018 U1 | * | 11/1999 |
| EP | 0 300 945 | | 1/1989 |
| WO | WO 96/00534 | | 1/1996 |

OTHER PUBLICATIONS

English Translation of Basic Abstract from DERWENT of DE 29915018 U1.*

* cited by examiner

*Primary Examiner*—Elizabeth L McKane
*Assistant Examiner*—Regina Yoo
(74) *Attorney, Agent, or Firm*—Browdy and Neimark, P.L.L.C.

(57) ABSTRACT

An apparatus is disclosed for sterilizing dental hand pieces 80. The apparatus comprises a treating chamber 22. Different channels 41-44 in bottom plate 36 of the chamber 42 connect the interior of the chamber and the hand piece 80 with saucers 62-68 of water pressurized air, oil and steam. The connection is effected through conduits arranged as channels in a metal block 50 and through valves arranged in a valve block 60. Accordingly, maintenance and mounting is easy. Moreover, safety switches 96 for the movement of the lid 4 of the chamber 22 are provided in a foil 90 arranged around the holding of the treatment chamber, which switches 96 are pressure sensitive membrane switches operating with elements 100 on the lid 4.

11 Claims, 11 Drawing Sheets

APPARATUS FOR STERILIZING DENTAL HAND PIECES

FIELD OF THE INVENTION

The present invention relates to an apparatus for sterilizing dental hand pieces, comprising a housing having a pressure resistant treating chamber with internal holding stub means for receiving a socket for one or more dental hand pieces.

DESCRIPTION OF THE PRIOR ART

Said holding stub means having through-channels for connecting exterior treatment fluid source means to internal standard channels in and through said hand pieces in order to enable a through-flushing of treatment fluid through these channels from a socket end to a tip end of said hand pieces.

These instruments are characteristic in having narrow, through-going channels for cooling water and for either a rotary driving shaft for a drilling head or for an air flow for driving a turbine. A need has arisen for effecting a complete sterilization of these instruments between uses for successive patients, and different apparatus systems for this purpose have already been developed, see for example EP-B-0,300,945 and U.S. Pat. No. 5,552,113.

In connection with the invention special attention is paid to the system type, in which the instruments are subjected to autoclaving, preferably after a flush cleaning of the said channels. By the autoclaving and the associated generation of steam the exterior surfaces of the instruments will be effectively sterilized, but an effective sterilization of the said channels will not be automatically effected thereby.

According to U.S. Pat. No. 5,552,113 it is proposed to feed the steam into the autoclaving chamber by forcing the steam through the said channels from an exterior steam generator, but even though the channels may thereby be effectively sterilized, the general autoclaving of the instruments will be inferior to what is achievable in an ordinary autoclave, where the steam is generated inside the treating chamber, in which the sterilizing effect, widely due to condensation on the instruments, is more pronounced. Such a "primary" autoclaving with internal steam generation is known from WO 96/00534, where the inlets to the said channels in relevant instrument holders or adapters are used for letting in of flushing water, whereby this flushing water is collected in the treating chamber and subsequently heated inside that chamber for primary steam generation therein.

It has been recognized that the said inlet to the narrow channels, normally constituted by a holding stub sealingly communicating with the channels at the handle root end of the instrument and, itself, being connected with relevant supply sources through pipe or hose means, may alternatively be used as an outlet, namely by a forcing out of autoclave steam from the treating chamber through the narrow channels. This may be arranged without any kind of connector means between the treating chamber and the free tips of the instruments since these, as far as the steam is concerned, will be inherently exposed to the steam pressure inside the chamber. Of course, any inlet connection in the holding stub, if also used for outlet purposes, should be connectable to the relevant channel means through a valve system for connecting the channel means selectively to an inlet medium source or to a drain outlet.

It has also been proposed to use an external steam generator, preferably mechanically built directly together with the treating chamber and delivering the steam directly into the treating chamber. This has been effected through pipe or hose connections between the steam generator and each of the instrument holding stubs. Additionally, the delivery of the steam from the external steam generator, in which the steam temperature and pressure can be brought up to a relatively very high level, will condition a high degree of temperature control with respect to the temperature of the steam as passing through the said channels, insofar as any relevant temperature sensor can be placed in the treating chamber itself and not in connection with the channels or associated steam supply pipe means.

It has been a common drawback associated with known apparatuses that they are difficult to assemble and that they are difficult to maintain due to a large number of connections between different elements especially different pipes for connecting the stub means with the steam generator and with sources for treatment fluid which could encumbrance water, oil, solvents and other fluids. Moreover a rather high pressure exists in the system which involves a risk for leakage in the connections between different pipes.

Furthermore the safety switches connected with the lid comprise several individual switches which are time consuming to mount and to maintain. The prior art apparatuses comprise a main board arranged within the housing. This board is difficult to access and there is a risk of break down due to liquid and vapor impact on the elements arranged on said board.

SUMMARY OF THE PRESENT INVENTION

It is an object of the present invention to provide an apparatus which overcomes or at least substantially reduces the serious drawbacks associated with known apparatuses, such as those discussed above.

It is another object of the invention to provide an apparatus which is easy to maintain and which is reliable in use due to a limited number of elements which could fail or break down.

According to the invention this is obtained with an apparatus comprising:

a removable lid for closing an entrance opening of the chamber first conduit means to connect said holding stub means to an exterior treatment fluid source to enable a through-flushing of treatment fluid through channels in said hand pieces from the socket end to a tip end of said hand pieces, second conduit means to connect a steam generator with said treatment chamber having one or more outlet openings for steam, and outlet valve means which are arranged in said conduits and which connect said holding stub means to the exterior atmosphere so as to enable back-flushing of pressurized steam from said treating chamber from the tip end through the channel to the socket end thereof.

According to a first embodiment of the inventive apparatus said holding stubs are provided with at least two through-channels for selectively supplying treating fluid to at least two different internal channels of said instruments, said outlet valve means being operable to effect steam back-flushing through the individual channels in an alternating manner through one through-channel at a time.

According to a further embodiment of the inventive apparatus the lid is mounted on a holder ring supported by extendible carrier rods which extend through the housing to a drive system arranged in the housing beneath the treating chamber which drive system comprises a drive belt driven by a motor and an belt fastener incorporating a spring which urge a roller against the belt to obtain correct fastening in the belt running around toothed wheels on the carrier rods and the motor.

Hereby an identical and correct fastening of the drive belt for the lid movement is automatically ensured.

According to a further embodiment of the inventive apparatus said removable lid is provided with safety switches to ensure correct operation, said switches are provided as pressure sensitive membrane switches mounted in a foil arranged around the annular outer area of the lid surrounding the opening of the treating chamber, which membrane switches cooperate with a power supply for the movement of the lid. Preferably, an annular ring is arranged movably up and down in a position above the upper annular area along the entrance opening of the treating chamber forming an annular space there between in which said foil is arranged. Hereby the foil is arranged in a protected position and a secure operation is obtained.

According to a further embodiment of the inventive apparatus said conduits are arranged as channels in metal blocks arranged in said housing. Hereby a simple construction is possible.

According to a still further embodiment of the inventive apparatus a top plate of the housing is arranged above wall profiles, wherein stays are secured to a bottom plate and extend to the top plate and wherein the top plate is releasably attached to the stays through springs being urged behind protrusions arranged at the top of the stays. This makes it possible to open the housing without the need of overturning the apparatus to get access to screws which are used to secure the stays to the bottom plate. In order to meet a requirement for use of tools to demount the top plate it is possible to arrange a single quarter turn screw at the back side of the apparatus.

According to a still further embodiment of the inventive apparatus said housing is divided into a first and a second section, wherein said treating chamber and said conduit means are arranged in said first section and wherein the second section which contains a main electronics board is hinged to a back plate of the first section and comprises metallic walls. Hereby the risk of break down due to impact from water and vapor is obviated and moreover an electrical maintenance of the main board is eased.

The access to the second section is easily obtained by unscrewing screws by which the second section is secured to the housing. In an especially simple construction the second section is formed between an outer side of the tank profile and a metallic back plate hinged thereto.

Furthermore, a fan which is arranged for venting the housing is placed in a fan plate between the first section and the second section whereby cold air flows through the second section and is blown into the first section. Hereby it is secured that cold air is drawn through the fan and moreover the position of the fan in the middle of the apparatus reduces noise.

According to a still further embodiment of the inventive apparatus it comprises a control panel including a membrane switch keyboard and a LCD display in stead of push buttons and seven segment display. Hereby the apparatus is easier to clean. Moreover it is possible to have a control system in which it is easy to add new features to a menu in stead adding push buttons to the control panel. Moreover the panel is easily mounted simply by gluing the panel to a top plate of the housing.

According to a still further embodiment of the inventive apparatus means are provided for supplying a cleaning liquid such as water to build up a bottom layer of the liquid in the treating chamber, and in which the bottom of the treating chamber has a number of upwardly directed air nozzles connected with an external source of compressed air through valve means operable to admit the compressed air to said nozzles in a pulsating manner to effect liquid splashing against the exterior of the instruments as held in positions above said liquid layer.

In the following the invention is described in more detail with reference to the drawing, in which:

DETAILED DESCRIPTION OF THE PREFERRED EMBODIMENT

Figure 1:
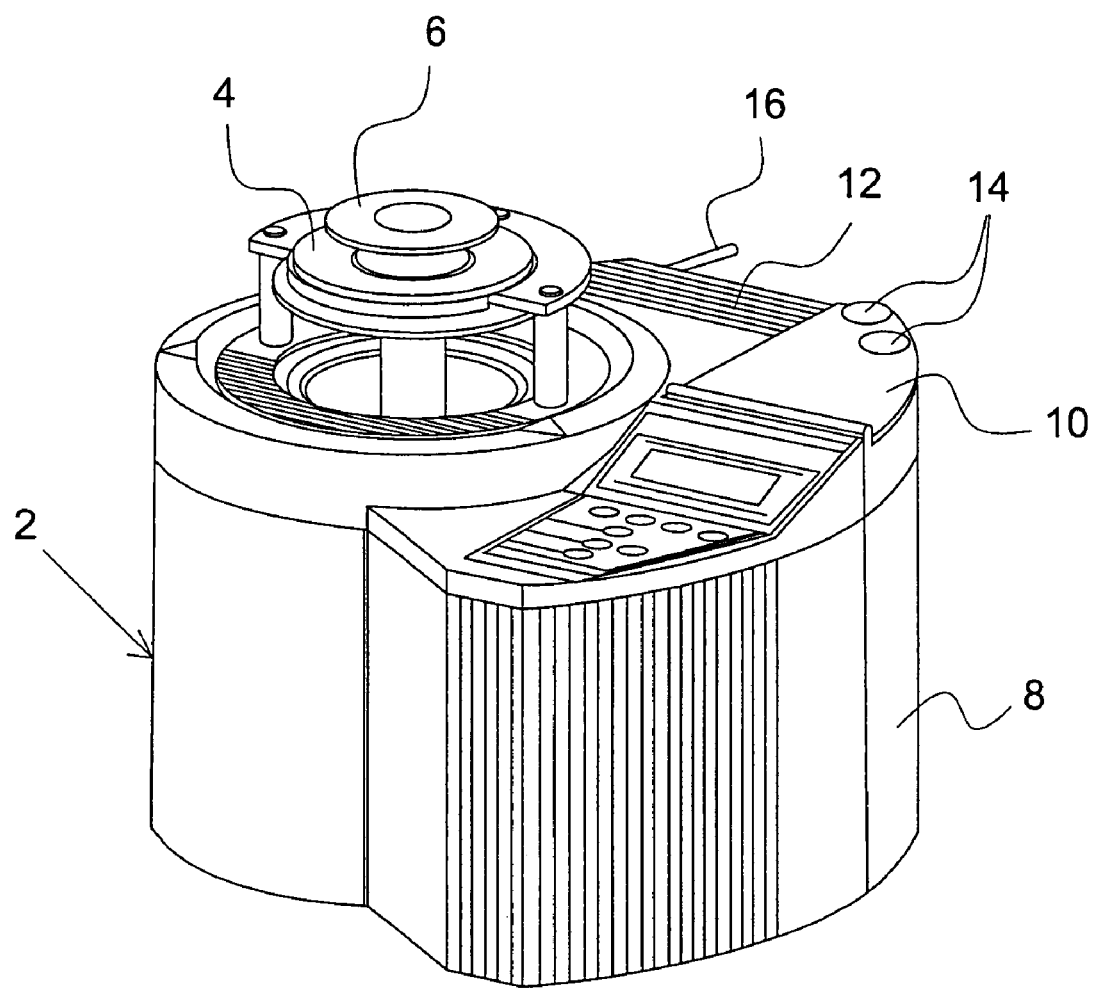
FIG. 1 is a perspective view of an prior art apparatus.
Figure 2:
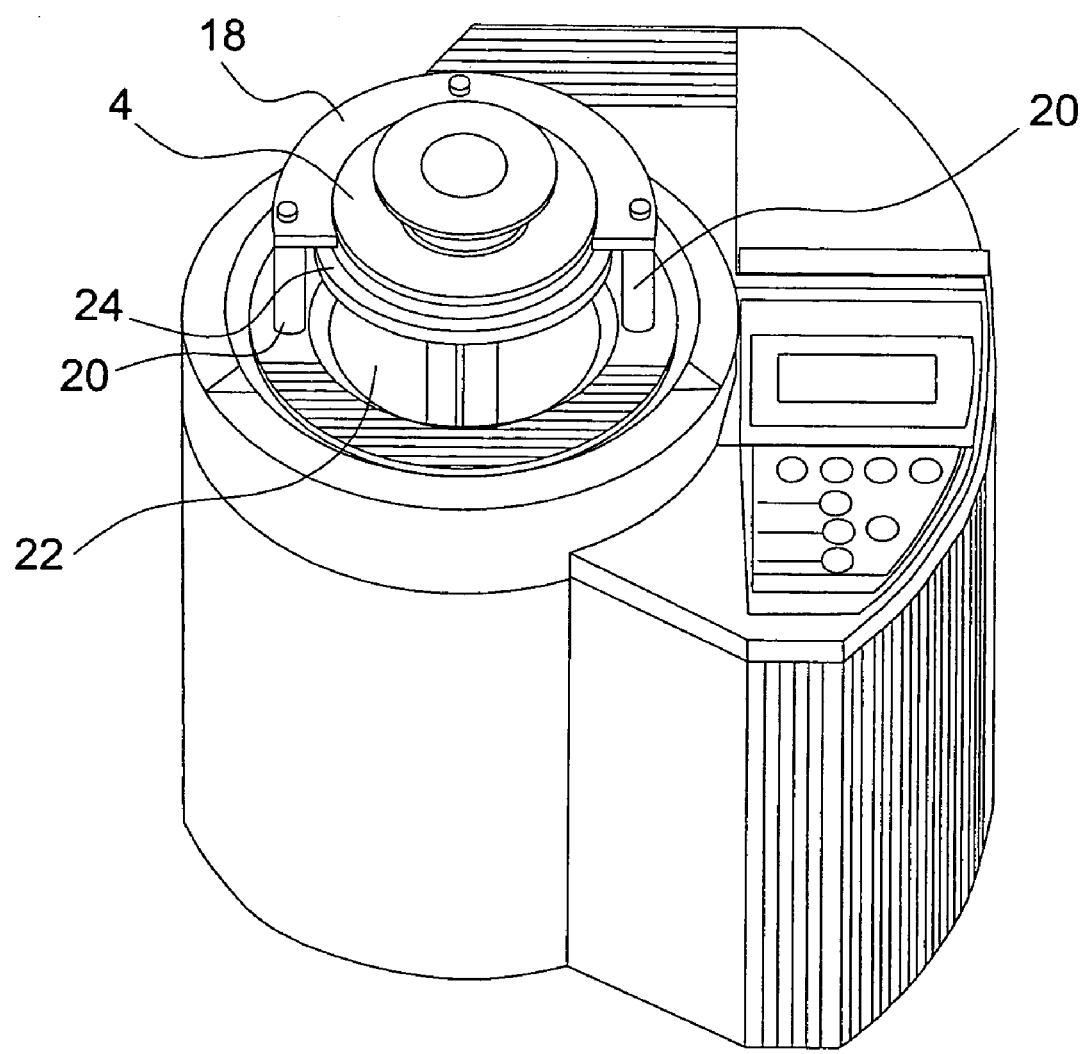
FIG. 2 is a similar view of a treating chamber thereof, shown in partly opened/closed condition.
Figure 3:
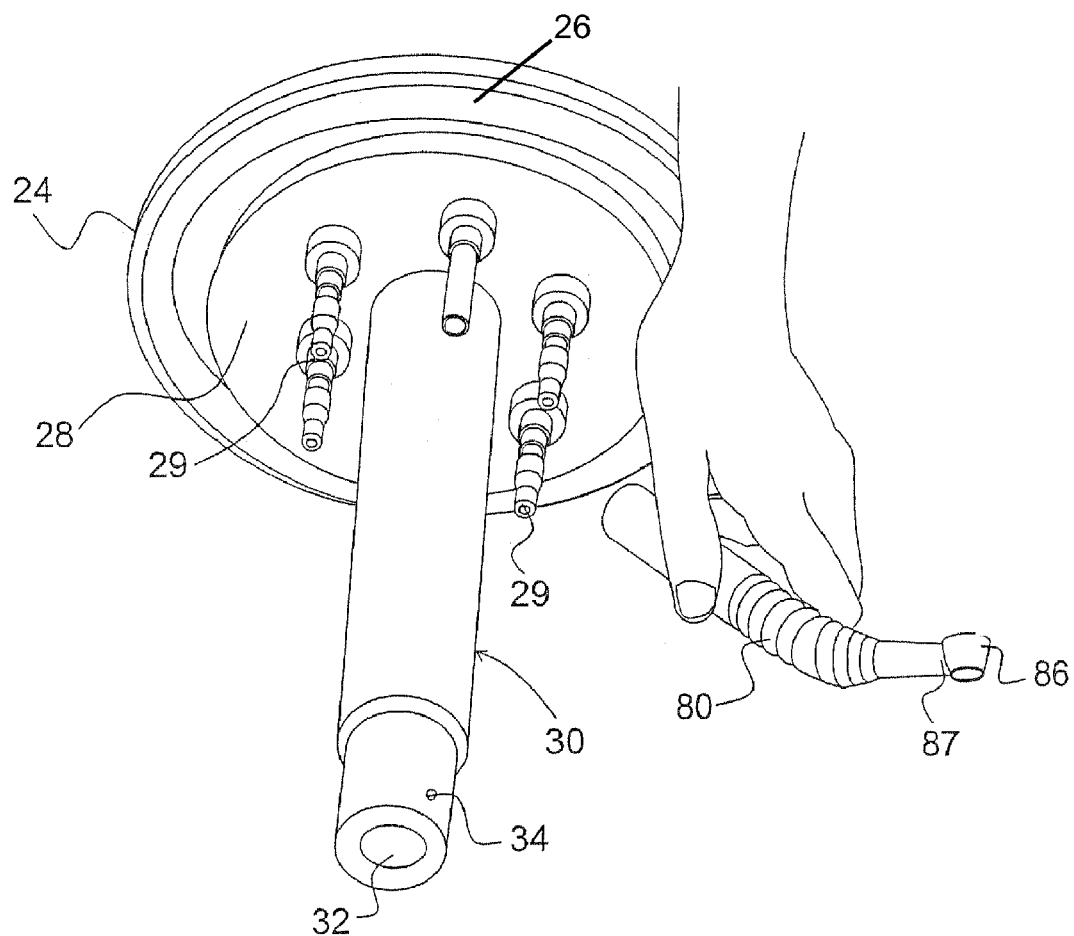
FIG. 3 is a similar view of an instrument holder thereof.

FIGS. 1-3 illustrate general elements which the apparatus according to the present invention have in common with the prior art apparatus.

FIGS. 4-11 illustrate an embodiment of the apparatus according to the present invention. Elements which are identical or equivalent have are denoted with same reference number through all Figures.

The apparatus illustrated in FIG. 1 comprises a cylindrical treating housing 2 covered by a lid 4 with a handle knob 6 and being integrally connected with a electronic housing 8, a tank housing 10 and an operation housing 12 holding the relevant valve and other operational equipment. The tank housing 10 has removable lids 14 for providing access to tank units for water and oil, respectively. The operation housing has a stub 16 for hose connection with an exterior pressurized air system.

As indicated in FIG. 2 the lid 4 is mounted in a half-circular holder ring 18, which is connected with the treating housing 2 by means of three carrier rods 20, which can be raised and lowered by non-illustrated actuator means in the treating housing. The latter comprises a central, upwardly open treating chamber 22, which is tightly closable by a lower disc member 24 connected with the lid 4. The inner edge of the semi-circular holder ring 18 is received in an annular groove between the overlying lid plate 4 and the underlying disc member 24, such that the lid structure as a whole may be laterally displaced by a horizontal movement out of and into an operative position centrally engaged with the raisable/lower-able system 18, 20.

FIG. 3 shows that the lid disc member 24 has an outer sealing ring 26 for sealing against the top of the treating housing and a central block member 28 provided with an annular row of downwardly protruding adapters 29 for receiving the handle ends of the dental instruments. These adapter or connector stubs 29 are designed just as the corresponding stubs on their associated handle elements, with sealed ring zones enabling communication between parallel input channels (from above) and more or less parallel, internal channels in the instruments, when socket portions of these instruments are pushed into holding engagement with the stubs. The lid 4 is advantageous in that the knob 6 has a flat top surface. Hereby it is possible to place the lid on a table with the adapters orientated freely upward when inserting and removing instruments 80.

It is possible to interconnect a number of such holding stubs by means of a channel system inside a common carrier block 28 in such a manner that the relevant individual channels in the instruments will be connected in parallel, typically a central "driving" channel either for a mechanical driving shaft leading to a drilling head or for guiding a pressure fluid to a driving turbine in a drilling head, and an eccentric "spray" channel for guiding a cooling fluid to the drilling area.

Thus, only two main channels will be sufficient to communicate with all of the holding stubs, and in the assembly shown in FIG. 3 the block member 28 is provided with a downwardly projecting central rod 30, in which these channels are provided, ending inside a bottom socket opening 32 and a side socket opening 34. The channels in the rod 30 are connected with channels 161 (see FIG. 12) in a distribution plate 160 arranged at the lid 4.

The channels 161 are arranged in order to have a back pressure being high to ensure that oil is not accumulated in the lid. This is obtained by providing small orifices 162 creating a back pressure which many times higher than the back pressure of the instruments 80. Hereby the apparatus will function in the same way whether or not instruments are arranged at all connector stubs 29.

An important function is lubricating the instruments 80. This is established through the distribution of oil for the six connector stubs 29 through the channels 161 in the distributor plate 160. The oil is dosed by means of an electrically actuated pump which pumps a predetermined oil volume into the channels. Simultaneously, pressured air is blown into the oil channel. The air forces the oil forwards to the adapter in the bottom of the chamber 22 and through the oil channel 34 in the rod 30. Hereby it reaches the distributor plate 160 arranged at the lid 4. During this transport of the oil, a certain mixture of oil and air is established. Thereby the oil will become partly atomized, and accordingly it could be distributed more easily.

Figure 12:
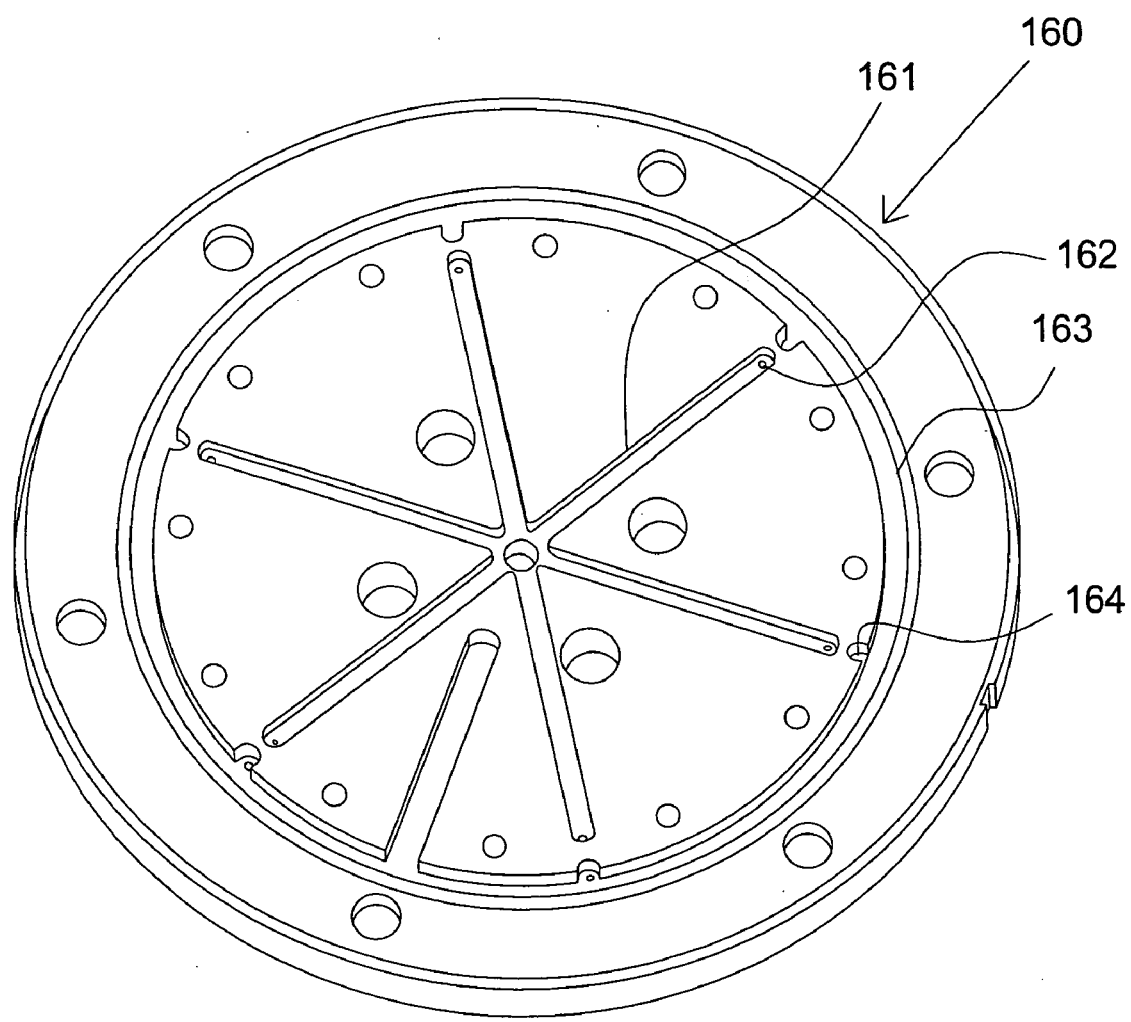
FIG. 12 is a perspective view of a disinfection plate.

The distributor plate 160 illustrated in FIG. 12 is a circular plate arranged to be connected to the lower side of the lid 4 facing against the chamber 22. The distributor plate 160 supports the connector stubs 29. In the illustrated embodiment, the distributor plate 160 is arranged for six connector stubs and is provided with six channels 161 extending from a central part to a part in a distance from the circumference at a position where the connector stubs are to be arranged. In the central part, a throughgoing hole is arranged from which connection is established to the six identical channels 161. An optimum distribution is ensured seeing that the entrance from the central hole to the channel is formed symmetrically, and the dimensions of the channels are adapted to the dimensions of the central hole. As indicated in FIG. 12, the channels are arranged radiating from the center. The orifices 162 at the end of each channel each comprise an orifice having a substantially smaller dimension than the cross-section of the channel 161. The distributor plate 160 comprises an eccentric hole being connected with an annular channel 163. At each of the connection points for the six instruments, an outlet 164 is arranged from the annular channel 163 through an orifice which has a substantially smaller dimension than the cross-section of the associated channel.

At the lower side of the distribution plate 160, it is possible to arrange adaptors/connector stubs for the instruments to be treated in the apparatus. Through such adaptor or stub, a connection is established between the oil channel in the distribution plate and the drive channel for the air motor in the instrument 80. Moreover, a connection is established from the annular channel of the distribution plate 160 to the spray channel of the instrument connected with the spray orifice 87.

Figure 4A:
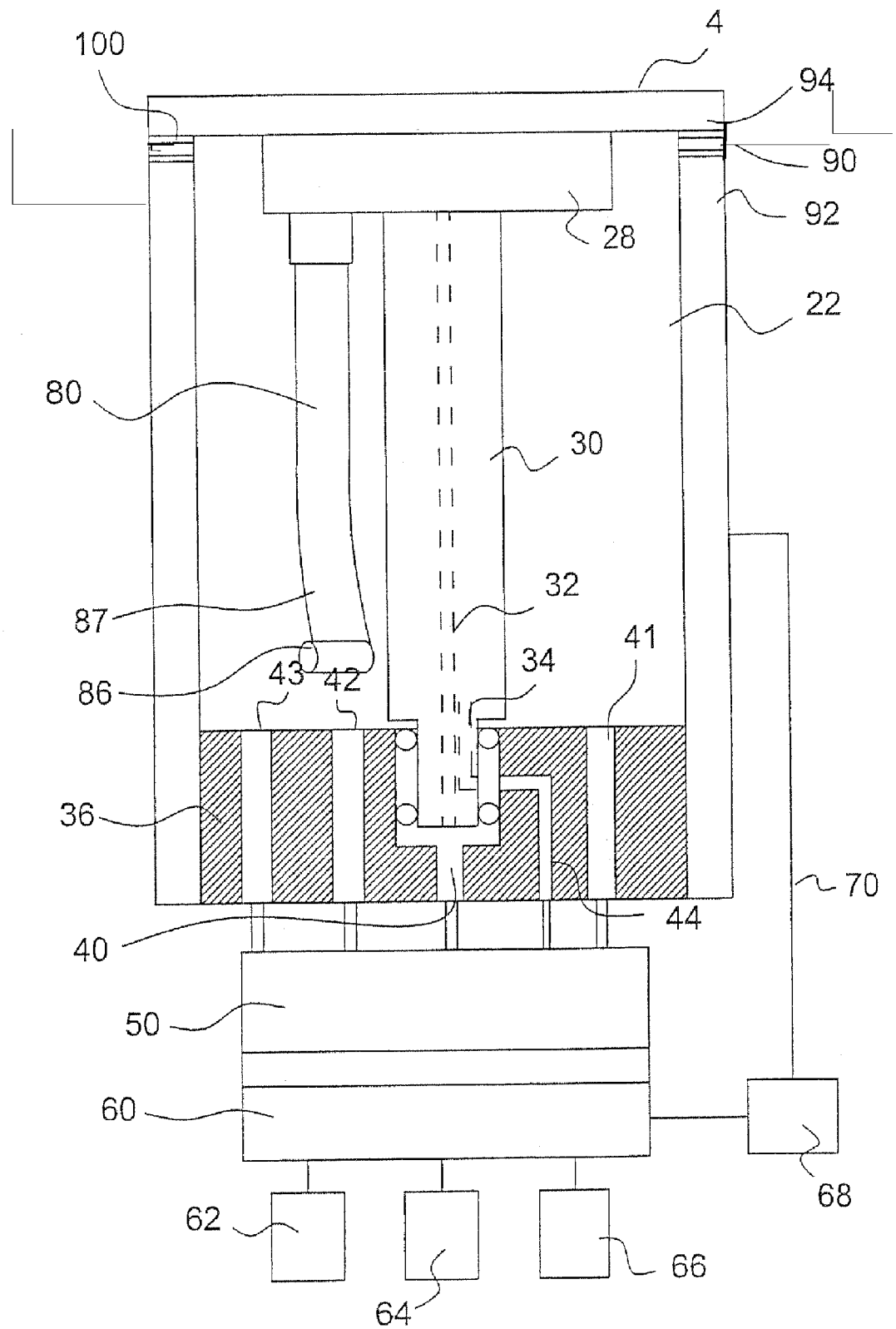
FIG. 4A is a diagrammatic view of an apparatus according to the present invention.
Figure 4B:
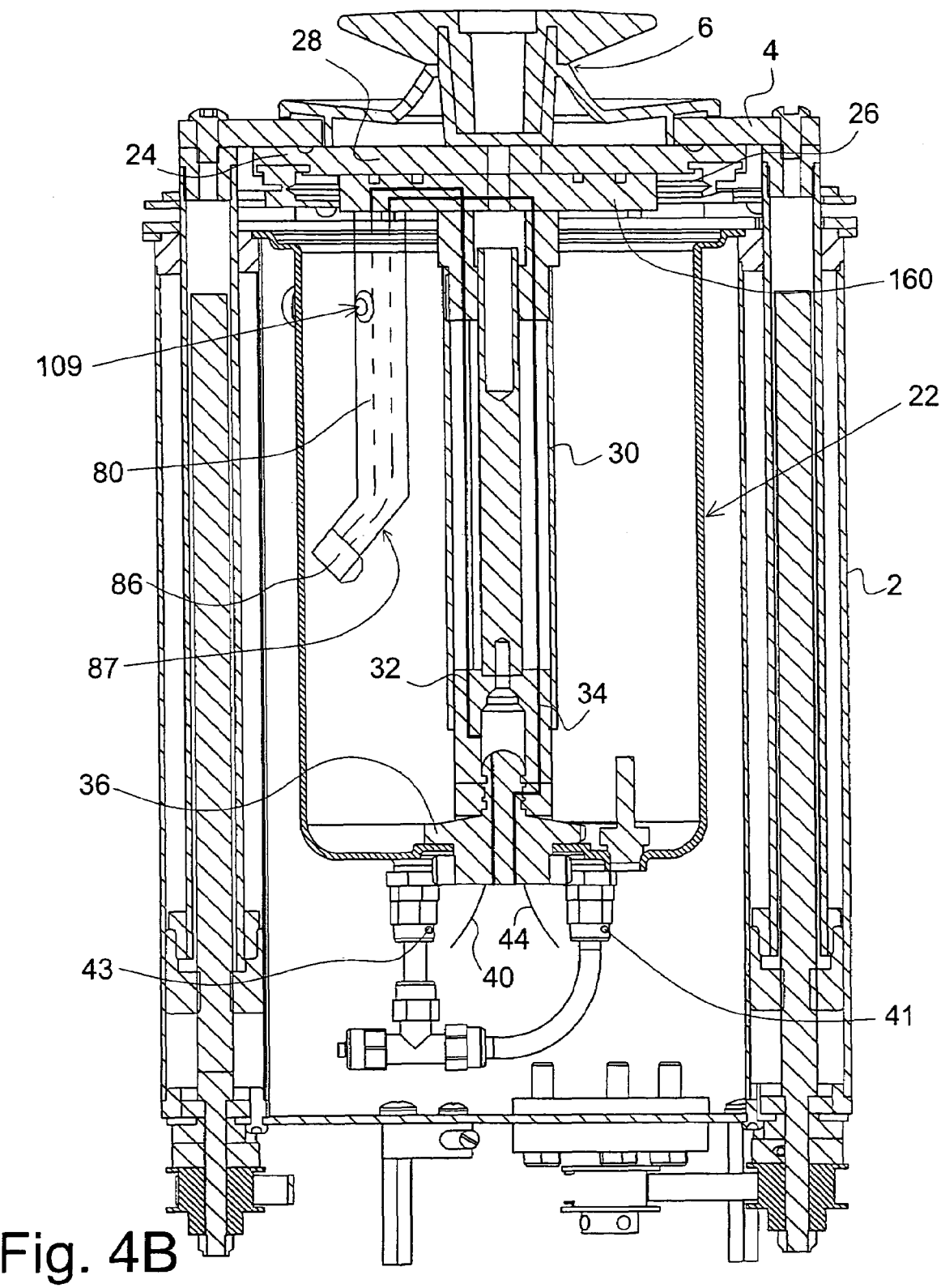
FIG. 4B is a more detailed view of the chamber corresponding to FIG. 4A.
Figure 5:
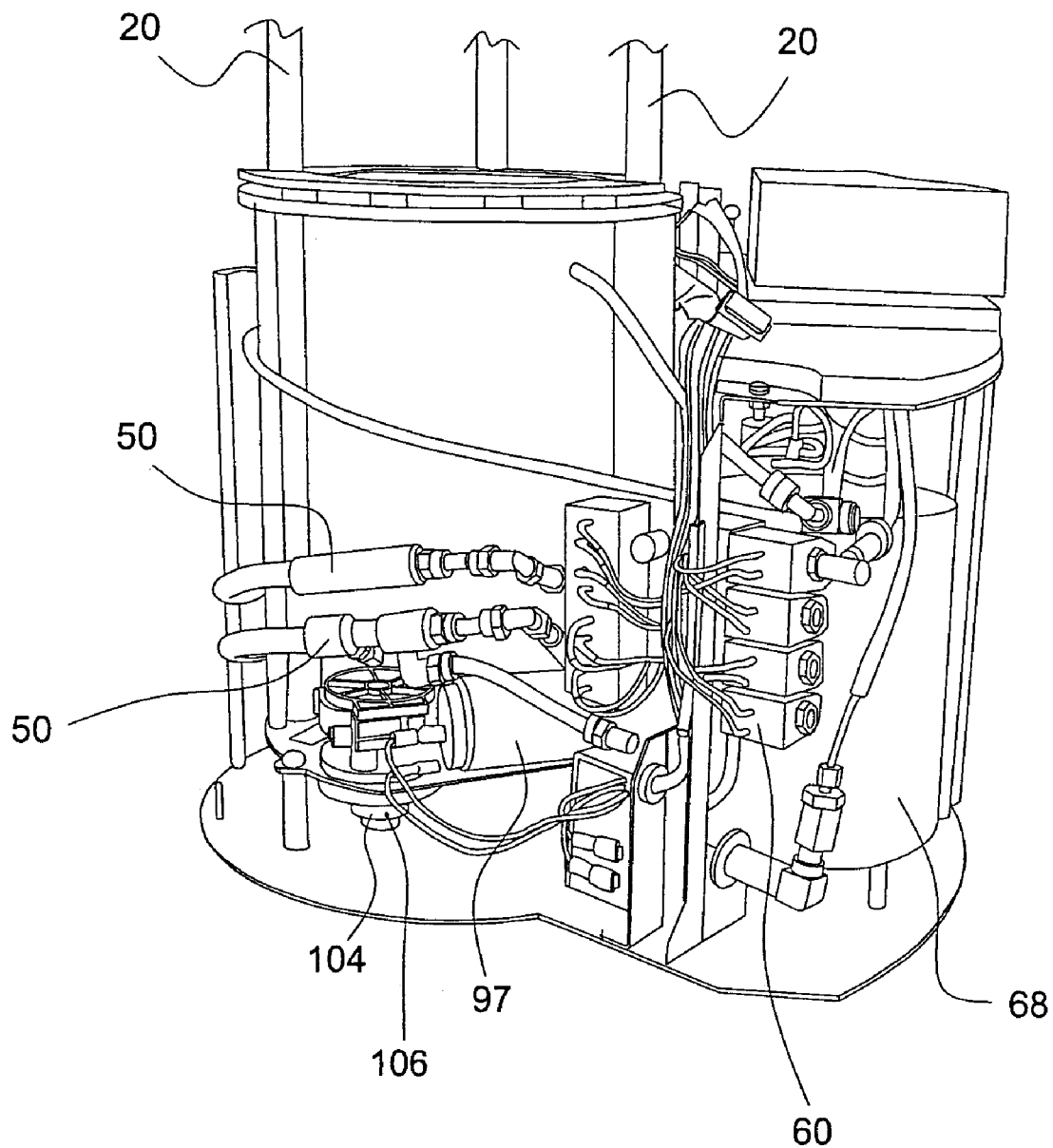
FIG. 5 is a perspective view of an apparatus according to the present invention.
Figure 6:
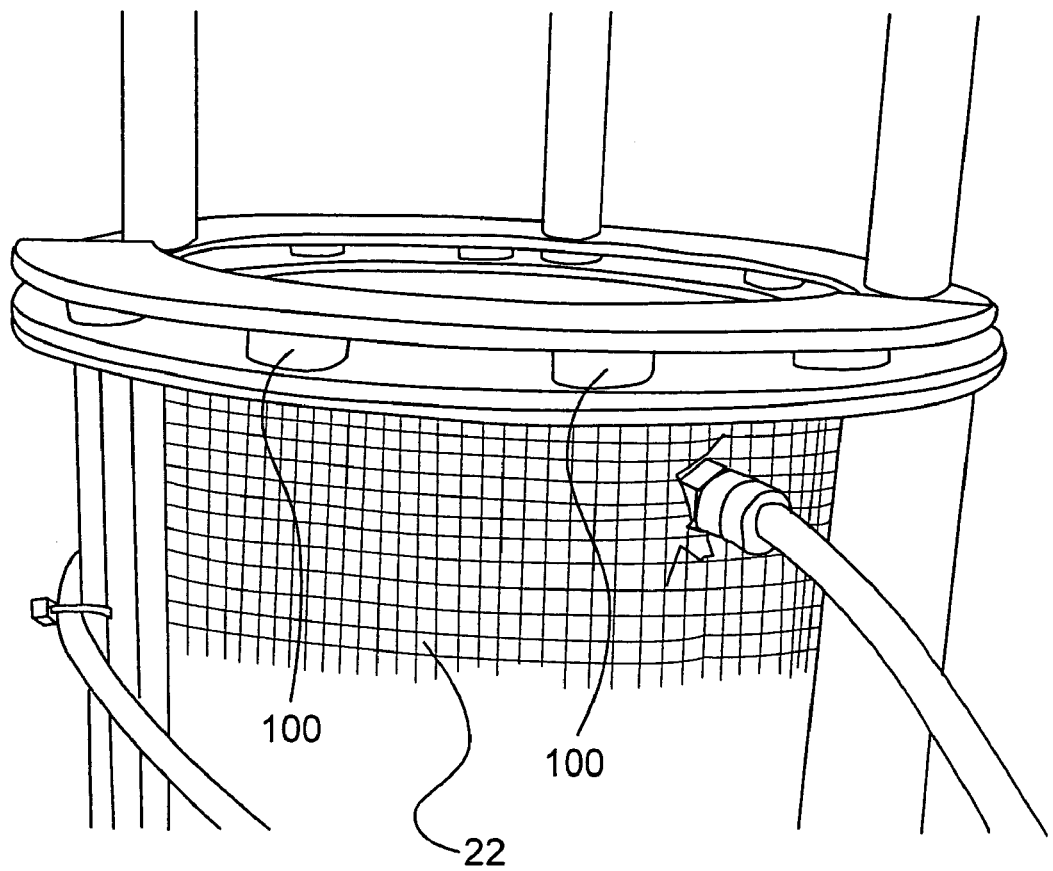
FIG. 6 is a partial perspective view of the apparatus illustrated in FIG. 5.

As shown in FIG. 4A and FIG. 4B, when the central rod 30 is lowered in connection with the lowering of the lid structure, the lower socket opening 32 of the central rod 30 will be connected to a through bore 40 in a fixed bottom plate 36 of the chamber 22. The side socket opening 34 is connected to a through bore 44. The bottom plate 36 comprises further bores 41-43 opening into the chamber 22 and arranged to direct different fluid into said chamber.

FIG. 4A shows how the bores 40-44 are connected via a channel block 50 containing conduits for connecting the stub means 29 and the treating chamber 22 to respective valves in a valve block 60 which is in turn connected to a source 62 of compressed air, to a source 64 of water, to a source 66 of oil and to a steam generator 68, which is also connected to the treating chamber 22 through a conduit 70.

In FIGS. 4A and 4B it is shown that a relevant dental instrument 80 is mounted on a selected holder and connector stub 29, which is not illustrated in FIG. 4B however it is illustrated in FIG. 3. This instrument 80 having interior channels for driving air to a turbine in a drilling head 86 and cooling water to a spray orifice 87, respectively. Through the upper block member 28 and the channels in the rod 30 the interior channels of the instrument will be connectable with the bores 40 and 44.

In FIG. 4B it is illustrated that the instrument 80 comprises an over pressure outlet/valve 109. Moreover it is illustrated that the lid 4 comprises the distributor plate 160.

The apparatus illustrated in FIG. 5-11 comprises an outer housing identical with the housing 2 illustrated in FIGS. 1 and 2. The apparatus would also comprise a lid member corresponding to the lid member 24 illustrated in FIG. 3. Moreover, the apparatus according to the present invention comprises connections, channels, valves etc. as illustrated in FIG. 4.

Figure 7:
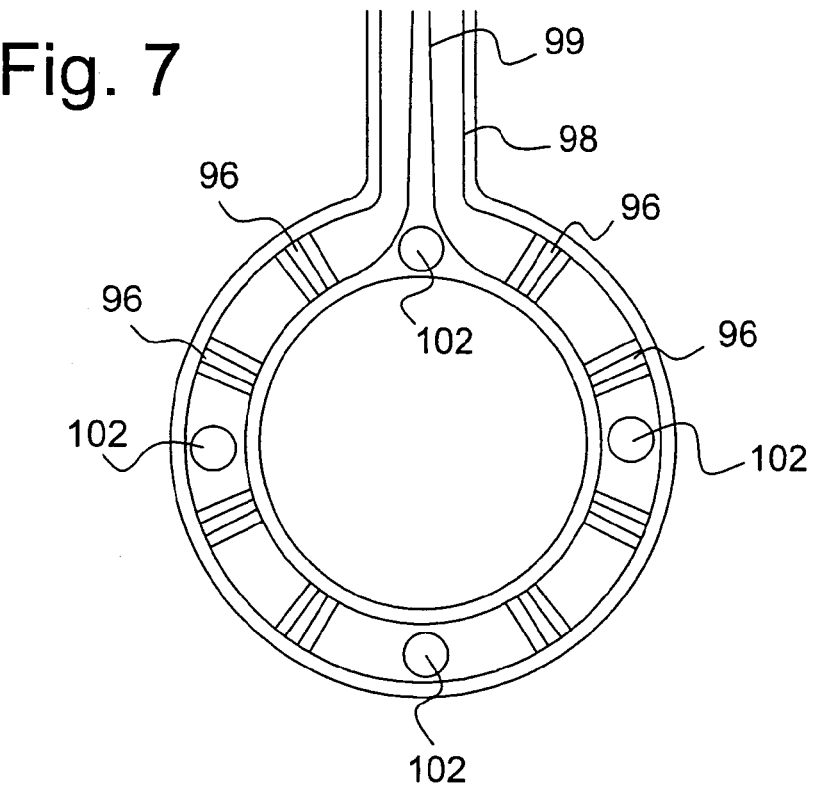
FIG. 7 is a view of a foil incorporating membrane switches.

The apparatus illustrated in FIGS. 4-11 differs from the apparatus illustrated in FIGS. 1-3 in that it comprises a foil 90 arranged between the upper side of the side wall profile 92 and an annular outer area 94 of the lid 4 which is illustrated more clearly in FIG. 7. The foil 90 comprises membrane switches 96 which through conduits 98, 99 operate the power supply (not illustrated) for a motor 97 (see FIG. 5) which drives the carrier rods. Hereby it is possible to stop the movement of the lid 4 when actuating member 100 (see also FIG. 6) activates the membrane switches 96. As illustrated in FIG. 7 the foil 90 is provided with openings 102 corresponding to the position of the carrier rods 20.

Figure 8:
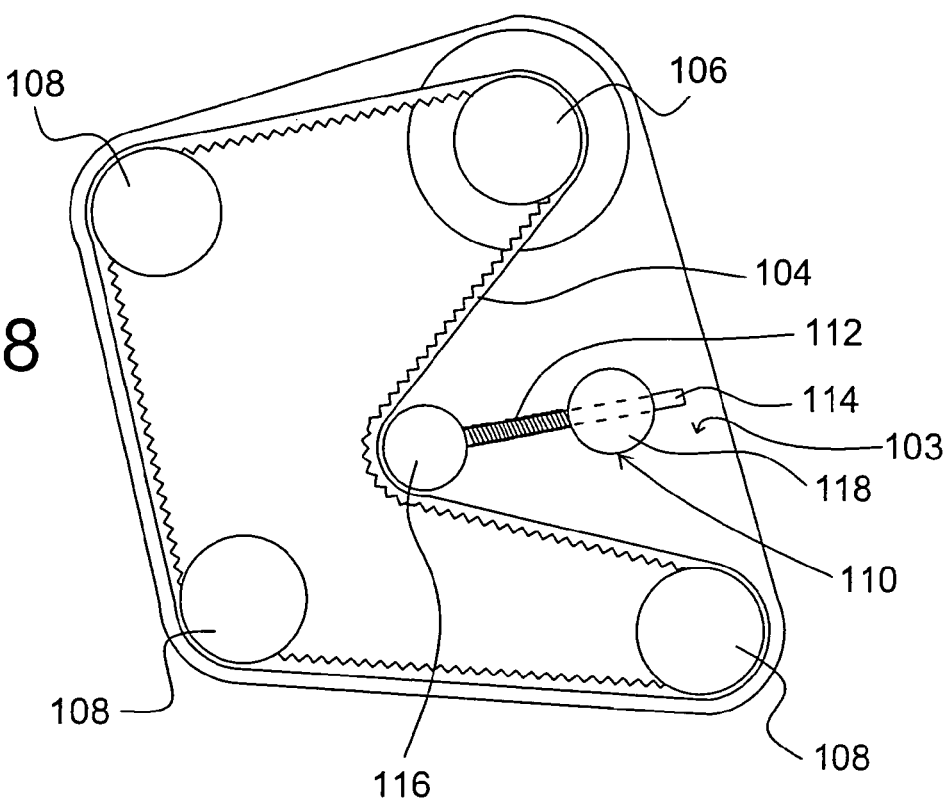
FIG. 8 is a view of the drive system for driving carrier rods.

FIG. 8 illustrates the drive system arranged under a mounting plate 103 below the treating chamber 22. The drive system comprises a tooth belt 104 driven by a wheel 106 connected to the motor 97 illustrated in FIG. 5. The belt 104 runs around wheels 108 connected with each of the carrier rods 20. The drive system comprises an automatic belt fastener 110 incorporating a spring 112 arranged around a rod 114. The rod connects an idle pulley 116 with a stud 118 fixed to the mounting plate 103. The spring 112 will exert a given force thereby ensuring a desired tension in the belt.

Figure 9:
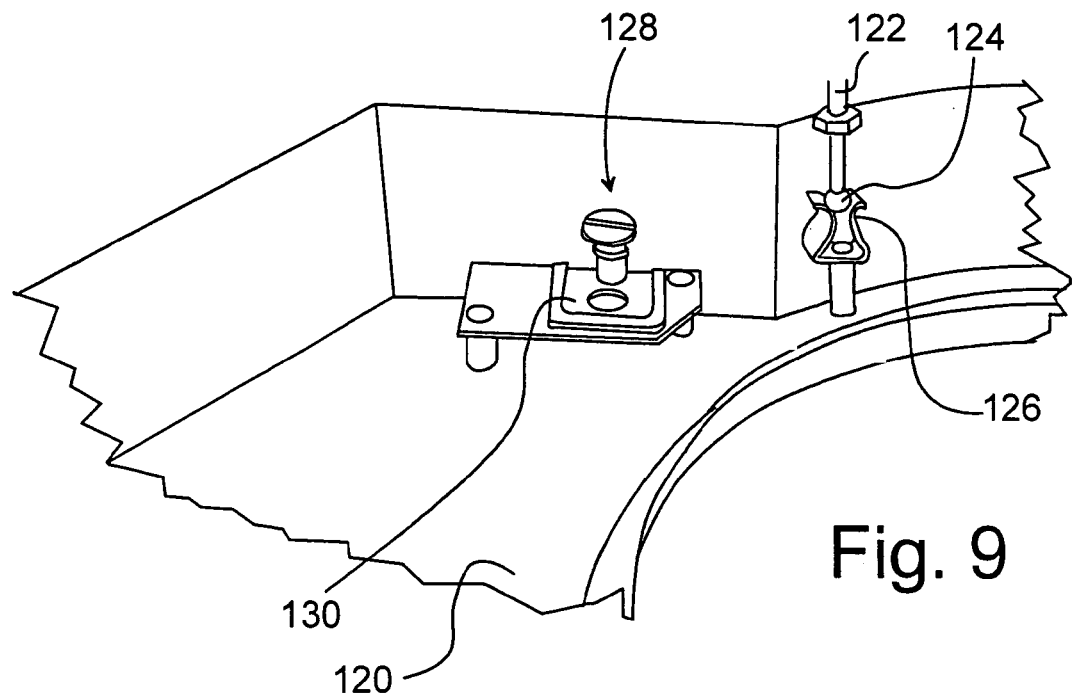
FIG. 9 is a partial perspective view of the under side of a top plate of the apparatus.

FIG. 9 illustrates a part of a top plate 120 of the housing which is arranged above the wall profiles. The top plate 120 which in FIG. 9 is shown upside down is connected through stays 122 having an enlarged head 124 which is releaseably maintained in an U-formed spring 126 mounted in a top plate 120. A suitable number of stays for instance between 4 and 8 may be used to attach the top plate. In countries where national regulation requires the use of tools to remove the top plate a single quarter turn screw 128 could be arranged at the back side of the apparatus. This screw 128 could be connected to a plate 130 fixed to the top plate 120 with a flange from a side wall profile positioned between the screw 128 and the plate 130.

Figure 10:
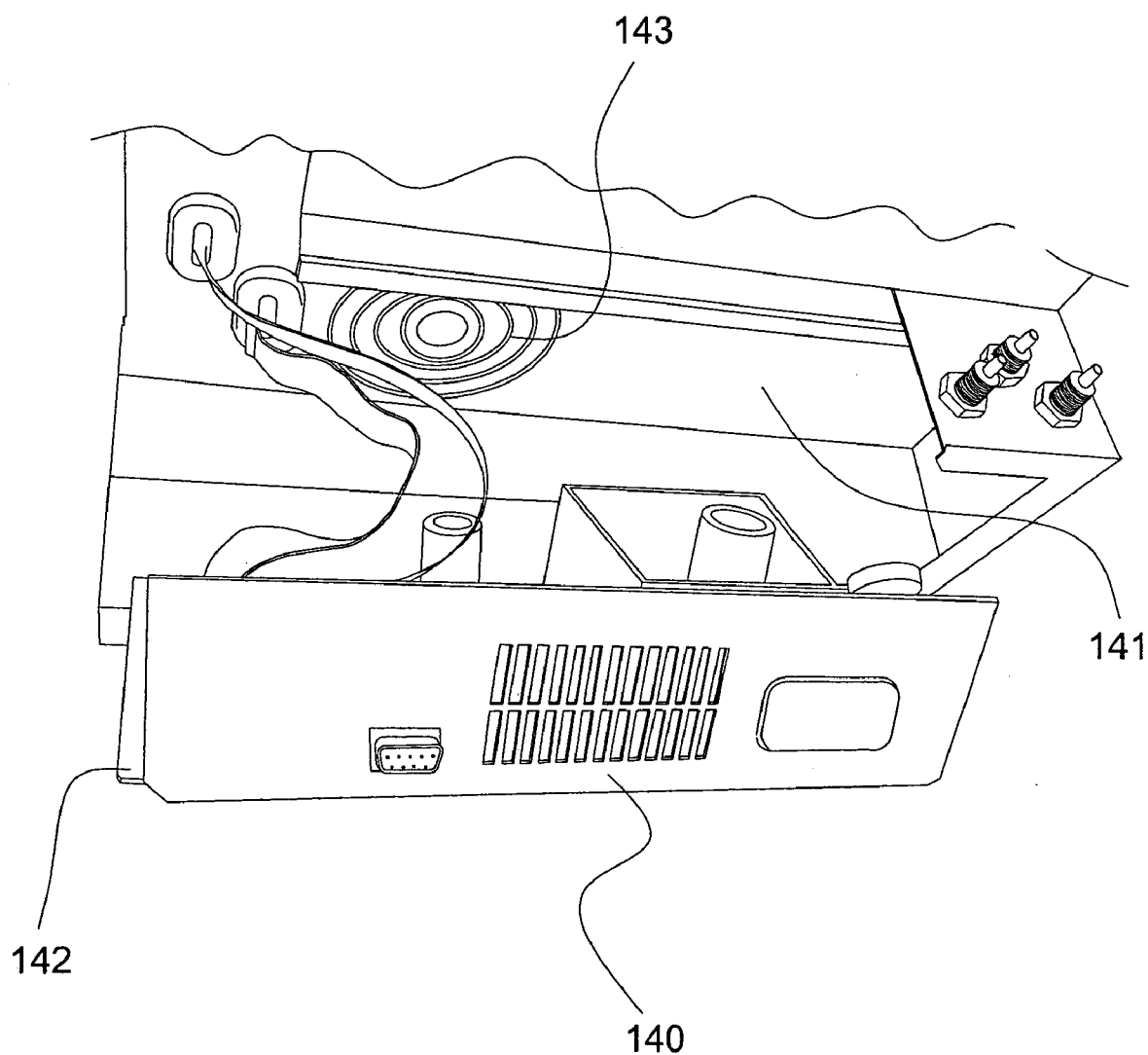
FIG. 10 is a partial perspective view of the apparatus seen from the back side.

FIG. 10 illustrates that a back plate 140 is hinged to a tank profile 141. The back plate 140 supports a main board 142 (only partly illustrated). Between the profile 141 and the back plate 140 a second section is arranged which is outside a first section which is disclosed in open state in FIG. 5 and which comprises the treating chamber, the conduit means, valve means etc. A fan 143 is arranged in the profile 141 in a position between the first and the second section. Hereby cold air is drawn through the second section and thereby provides a cooling effect for the main board and the treating chamber 22 arranged in the first section.

Figure 11:
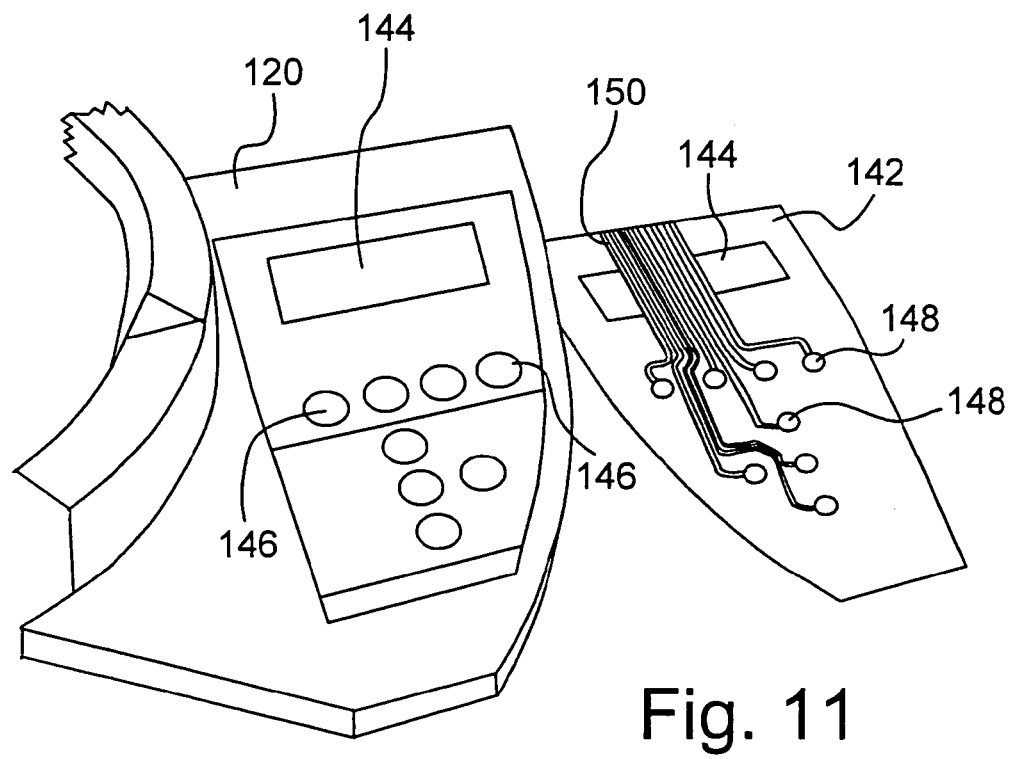
FIG. 11 is a partial perspective view of the apparatus seen from the top side.

FIG. 11 illustrates in the left-hand side a control panel arranged on the top plate 120 of the housing. In the right-hand side there is an illustration of a foil 142 seen from below which is used in the control panel 140. The control panel comprises an LCD display 144 and buttons 146 for activating membrane switches 148 arranged on the foil. The switches 148 are, through conduits 150, connected with the main board 142 in order to control and register the operation and different parameters involved in the sterilizing process.

In operation, the following steps are to be effected:
1. Mount socket portions of instruments 80 on holder stubs 29 in raised position of lid 4, with or without the lid structure being laterally released from the holding ring member 18. Press an operation start button when instruments are mounted and lid 4 is centered so as to be lowerable into its closed position according to FIG. 4.
2. Actuate water supply for effecting water flushing through both pairs of rod and instrument channels, respectively. Hereby both of the channels 82 and 84 are cleaned by water flushing, but it has been found that this cleaning is enhanced when it is effected as a pulsating series of water and air flushing, and for this reason valves are operable to connect the channels with the source 62 of compressed air, such that the desirable pulsation between water and air is achievable e.g. 3-5 times.
3. By the latter operation some amount of water will have entered the treating chamber 22, and it is desirable, at this stage, to effect a rapid pumping or pressing out of the potentially contaminated water. For this purpose a bottom outlet valve is opened, and at the same time the pressurized air from the source 62 is let into the treating chamber 22, such that the collected water in the chamber 22 will be forced out through a drain channel.
4. The oil is supplied so as to supply a small volume of oil, whereafter a valve is opened so as to permit compressed air to blow the oil volume through the relevant channels and into the drive channel 82 of the instrument(s).
5. Then a desired amount of water into the treating chamber 22. Then a valve is actuated intermittently so as to cause pulses of compressed air to blow up through a number of channels provided in the bottom plate 36 in an annular row, whereby the water is splashed up against the instruments. This pulsating cleaning operation is continued through a user-defined period of time.
6. Operation 2 is repeated.
7. Operation 3 is repeated.
8. Then steam is injected into the chamber 22 through channel 70. The air inside the chamber 22 will be displaced out through a venting valve.
9. At some 107° C. all air will have left the chamber 22, and the venting valve is closed. The steam generation is continued so as to build up temperature and pressure in the chamber 22.
10. When a preset temperature/pressure, e.g. 134° C./2.1 bar, has been reached, outlet valves are opened and closed in an alternating manner, where-by for each opening the high pressure in the chamber 22 will force out steam through the respective instrument channels 82 and 84 from the outer ends thereof and through the respective rod channels via the valves to a drain. This causing air pockets in the instrumental channels to be driven out. During each opening sequence the pressure in the chamber 22 and therewith the temperature will drop somewhat, and before the next opening sequence it is ensured that the steam generator re-establishes the 134° C. in the chamber 22. Preferably, each of the channels 82 and 84 is subjected to such a blow-through of steam four times.
11. After the last operation of step 10 the chamber 22 is again steam heated to 134° C., and this temperature is maintained for as long as required, not less than 3 operation minutes for 134° C. program.
12. Operation 10 is repeated.

After the last through-flushing the outlet valve is opened to allow steam and condensate to be drained from the chamber 22. When the temperature therein drops to e.g. 104° C. and the overpressure is less than 0.1 bar, the lid 4,28 and therewith the instruments 80 is lifted by actuation of the actuator means for raising the rods 20, and a new operation cycle can be initiated upon removal of the sterilized instruments 80.

During operation, the distribution plate 160 will have the following functions:

During internal wash, the instrument is washed with water. The water is driven out by means of air. Flushing is repeated a number of times in both channels simultaneously. Seeing that a larger backpressure will exist through the small orifices at the outlet from the channel, it is possible to flush every individual instrument in an optimal way independent of the number of instruments being mounted in the apparatus.

During Drying:
After the internal wash has been effected, the instrument will be dried by means of pressured air. The distribution plate 160 will split the flow of air in parts/flows independent of the number of instruments mounted at the distribution plate 160.

During Lubricating of the Instruments:
Seeing that the outlet from each channel is an orifice being substantially smaller than the channel, this would be the part of the system where the largest resistance exists. The orifice is smaller than the opening through the adaptor/stop and the instrument. Accordingly, there is no influence on the distribution of oil to each instrument whether an adaptor or instrument is arranged at the six positions or only at some of the six positions arranged in the distribution plate 160.

During Back Flushing:
During back flushing steam is led from the chamber of the apparatus trough the instrument 80 into the channels 161 of the distribution plate 160. Back flushing is effected separately for the two set of channels in the distribution plate 160. The form of the distribution plate 160 ensures an equal distribution of steam in all instruments independent of the number of instruments and/or adaptors which are mounted at the distribution plate.

During sterilization by autoclaving the instrument is sterilized through the hot steam which is conducted into the chamber 22. During the sterilization process, the temperature and pressure is monitored.

As it occurs from the above, the distribution plate 160 ensures that oil will be distributed equally to the six instruments, and the amount of oil to each instrument is independent of the number of instruments and/adaptors arranged at the distribution plates/lid. Hereby it is possible to optimize the amount of oil which is advantageous for the instruments and the environment.

We claim:

1. An apparatus for sterilizing dental hand pieces, comprising a housing having a pressure resistant treating chamber with internal holding stub means for receiving a socket for one or more dental hand pieces, and comprising:
   a removable lid for closing an entrance opening of the chamber,
   a carrier block having a first surface connected to a surface of the lid, the carrier block being provided with the internal holding stub means,
   a distribution plate having a first surface connected to a lower side of the lid, and supporting said internal holding stub means,
   first conduit means to connect said holding stub means to an exterior treatment fluid source to enable a through-flushing of treatment fluid through channels in said hand pieces from the socket end to a tip end of said hand pieces,
   said first conduit means comprising channels provided in said distribution plate, each channel running from a common central opening outwardly towards a periphery of the distribution plate, and an orifice at an outer end of each channel to establish a back pressure many times higher than the back pressure of the instruments to ensure that the apparatus will function in the same way whether or not instruments are arranged at all holding stubs, each orifice having a substantially smaller dimension than the cross-section of each of the channels,
   second conduit means to connect a steam generator with said treatment chamber having one or more outlet openings for steam, and
   outlet valve means which are arranged in said conduits and which connect said holding stub means to the exterior atmosphere so as to enable back-flushing of pressurized steam from said treating chamber from the tip end through the channel to the socket end thereof.

2. An apparatus according to claim 1, wherein said holding stubs are provided with at least two through-channels for selectively supplying treating fluid to at least two different internal channels of said instruments, said outlet valve means being operable to effect steam back-flushing through the individual channels in an alternating manner through one through-channel at a time.

3. An apparatus according to claim 1, wherein the lid is mounted on a holder ring supported by extendible carrier rods which extend through the housing to a drive system arranged in the housing beneath the treating chamber which drive system comprises a drive belt driven by a motor and an automatic belt fastener incorporating a spring which urge a roller against the belt to obtain correct fastening in the belt running around toothed wheels on the carrier rods and the motor.

4. An apparatus according to claim 1, wherein said removable lid is provided with safety switches to ensure correct operation, said switches are provided as pressure sensitive membrane switches mounted in a foil arranged around the annular outer area of the lid surrounding the opening of the treating chamber, which membrane switches cooperate with a power supply for the movement of the lid.

5. An apparatus according to claim 4, wherein an annular ring is arranged movably up and down in a position above the upper annular area along the entrance opening of the treating chamber forming an annular space there between in which said foil is arranged.

6. An apparatus according to claim 1, wherein said conduits are arranged as channels in metal blocks arranged in said housing.

7. An apparatus according to claim 1, wherein a top plate of the housing is arranged above wall profiles, wherein stays are secured to a bottom plate and extend to the top plate and wherein the top plate is releasably attached to the stays through springs being urged behind protrusions arranged at the top of the stays.

8. An apparatus according to claim 1, wherein said housing is divided into a first and a second section, wherein said treating chamber and said conduit means are arranged in said first section and wherein the second section which contains a main electronics board is hinged to a back plate of the first section and comprises metallic walls.

9. An apparatus according to claim 8, wherein a fan which is arranged for venting the housing is placed in a fan plate between the first section and the second section whereby cold air flows through the second section and is blown into the first section.

10. An apparatus according to claim 1, which comprises a control panel including a membrane switch keyboard and a LCD display instead of push buttons and seven segment display.

11. An apparatus according to claim 1, wherein means are provided for supplying a cleaning liquid such as water to build up a bottom layer of the liquid in the treating chamber, and in which the bottom of the treating chamber has a number of upwardly directed air nozzles connected with an external source of compressed air through valve means operable to admit the compressed air to said nozzles in a pulsating manner to effect liquid splashing against the exterior of the instruments as held in positions above said liquid layer.

* * * * *